(12) United States Patent
Katase et al.

(10) Patent No.: US 8,583,217 B2
(45) Date of Patent: Nov. 12, 2013

(54) IN VIVO DRUG CONCENTRATION DISTRIBUTION MEASURING DEVICE, VARIABLE-WAVELENGTH FILTER USED FOR THE SAME, AND IN VIVO DRUG CONCENTRATION DISTRIBUTION MEASURING METHOD

(75) Inventors: Makoto Katase, Azumino (JP); Chiyoaki Iijima, Ina (JP)

(73) Assignee: Seiko Epson Corporation (JP)

( * ) Notice: Subject to any disclaimer, the term of this patent is extended or adjusted under 35 U.S.C. 154(b) by 504 days.

(21) Appl. No.: 12/571,690

(22) Filed: Oct. 1, 2009

(65) Prior Publication Data

US 2010/0086484 A1   Apr. 8, 2010

(30) Foreign Application Priority Data

Oct. 6, 2008  (JP) ................. 2008-259425

(51) Int. Cl.
*A61B 6/00* (2006.01)
(52) U.S. Cl.
USPC ........... 600/476; 600/407; 600/473; 600/160; 349/97; 356/53; 356/63; 356/64; 356/433
(58) Field of Classification Search
USPC ........... 600/160–182, 407, 473, 476; 349/97; 356/53, 63, 64, 433
See application file for complete search history.

(56) References Cited

U.S. PATENT DOCUMENTS 4,019,808 A * 4/1977 Scheffer .......................... 349/97
4,582,396 A * 4/1986 Bos et al. ...................... 349/180
5,689,317 A * 11/1997 Miller ............................ 349/97
(Continued)

FOREIGN PATENT DOCUMENTS

JP   2000-267127 A   9/2000
JP   2000-516504 A   12/2000
(Continued)

OTHER PUBLICATIONS

Gao, Xiaohu et al., "In Vivo Cancer Targeting and Imaging with Semiconductor Quantum Dots", Nature Biotechnology, vol. 22, No. 8, Jul. 18, 2004, pp. 969-976 and Supplementary Information (5 pages).

*Primary Examiner* — James Kish
(74) *Attorney, Agent, or Firm* — Harness, Dickey & Pierce, P.L.C.

(57) ABSTRACT

An in vivo drug concentration distribution measuring device for measuring, when a drug having an imaging function is administered, in vivo concentration distribution of the drug is disclosed. The device includes: a light source which casts light to a living body as a measuring target; a variable-wavelength filter which, when the light is cast to the drug from outside of the living body, the light emitted from the drug to outside of the living body becomes incident on and transmits light of a predetermined wavelength range, of an entire wavelength range of the incident light, and which is capable of changing the predetermined wavelength range; a photodetector unit which detects intensity of light made incident through the variable-wavelength filter and acquires intensity distribution of light emitted from plural positions on the measuring target; and a drug concentration calculating unit which calculates a concentration of the drug in accordance with the intensity distribution of the light at the plural positions on the measuring target acquired by the photodetector unit.

8 Claims, 13 Drawing Sheets

(56) References Cited

U.S. PATENT DOCUMENTS

| | | | |
|---|---|---|---|
| 6,081,734 A | 6/2000 | Batz | |
| 7,961,326 B2 * | 6/2011 | Martini et al. | 356/433 |
| 2005/0267326 A1 * | 12/2005 | Loeb et al. | 600/102 |
| 2007/0002276 A1 | 1/2007 | Hirohara et al. | |
| 2008/0039697 A1 | 2/2008 | Morishita | |
| 2010/0036203 A1 | 2/2010 | Nakaoka et al. | |

FOREIGN PATENT DOCUMENTS

| | | |
|---|---|---|
| JP | 2005-211355 | 8/2005 |
| JP | 2006-158547 | 6/2006 |
| JP | 2007-519487 | 7/2007 |
| JP | 2007-294214 | 11/2007 |
| JP | 2008-043396 | 2/2008 |
| JP | 2008-148791 A | 7/2008 |
| WO | WO2005-072792 | 8/2005 |

* cited by examiner

IN VIVO DRUG CONCENTRATION DISTRIBUTION MEASURING DEVICE, VARIABLE-WAVELENGTH FILTER USED FOR THE SAME, AND IN VIVO DRUG CONCENTRATION DISTRIBUTION MEASURING METHOD

Japanese Patent Application No. 2008-259425 filed on Oct. 6, 2008, is hereby incorporated by reference in its entirety.

BACKGROUND

1. Technical Field

The present invention relates to an in vivo drug concentration distribution measuring device, a variable-wavelength filter used for the same, and an in vivo drug concentration distribution measuring method.

2. Related Art

In medical fields, when a drug is administered to a patient, information on the concentration of the drug within the patient's body needs to be acquired in order to minimize any side effect of the drug and achieve satisfactory therapeutic effects. Traditionally, the most common technique is to collect blood from the patient's vein, measure the blood level and analyze the data, thereby analyzing in vivo pharmacokinetics. However, the blood level needs to be measured, for example, at five to six points of time in order to learn accurate pharmacokinetics. It is practically impossible to measure the blood level so many times in usual clinical practice and the measurement is limited to one to two points of time in view of guaranteeing therapeutic effects and safety. Thus, a method for acquiring in vivo drug concentration distribution by a non-invasive technique is required. Moreover, learning the in vivo drug concentration plays an important role not only in treatment but also in development of pharmaceuticals.

Traditionally, the following methods for leaning the in vivo drug concentration are proposed. JP-A-2007-294214 discloses a drug concentration measuring device having an organic sensor which measures in vivo drug concentration of a drug such as aspirin, and a body temperature sensor which measures body temperature. JP-A-2007-519487 discloses a system for adaptively adjusting drug administration. This system uses a technique of measuring changes with time in physiological actions of the patient when a drug is administered, including blood pressure, heart rate and body temperature, and thereby detecting drug concentration. JP-A-2005-211355, though not a technique of measuring concentration, discloses a lymphatic vessel observing device which casts a laser beam to an observation site after administering a contrast agent to a lymphatic vessel, and then detects near-infrared rays radiated from the contrast agent at the time, thereby percutaneously observing the lymphatic vessel.

However, none of the techniques disclosed in JP-A-2007-294214, JP-A-2007-519487 and JP-A-2005-211355 can meet the above needs.

In the technique disclosed in JP-A-2007-294214, when the organic sensor is used, it is necessary to needle a finger tip or the like by a needling device and thus attach blood to a test paper. That is, the technique disclosed in JP-A-2007-294214 can not measure drug concentration distribution by a non-invasive technique. The technique disclosed in JP-A-2007-519487 is to measure physiological actions of the patient when a drug is administered. Therefore, this technique has problems such as occurrence of individual difference in measurement results, poor reproducibility of measurement results, and the lengthy time required for measurement. The device disclosed in JP-A-2005-211355 can observe lymphatic vessels but cannot measure drug concentration distribution.

SUMMARY

An advantage of some aspect of the invention is that a drug concentration distribution measuring device that can accurately and quickly measure in vivo drug concentration distribution by a non-invasive technique, a variable-wavelength filter used for the device, and an in vivo drug concentration distribution measuring method can be provided.

According to an aspect of the invention, an in vivo drug concentration distribution measuring device includes: a light source which casts light to a living body as a measuring target; a variable-wavelength filter which, when the light is cast to a marker from outside of the living body, the light emitted from the marker to outside of the living body becomes incident on and transmits light of a predetermined wavelength range, of an entire wavelength range of the incident light, and which is capable of changing the wavelength range; a photodetector unit which detects intensity of light made incident through the variable-wavelength filter and acquires intensity distribution of light emitted from plural positions on the measuring target; and a drug concentration calculating unit which calculates a concentration of the drug administered with the marker in accordance with the intensity distribution of the light at the plural positions on the measuring target acquired by the photodetector unit.

The in vivo drug concentration distribution measuring device according to this aspect of the invention is a device which measures in vivo concentration distribution of a drug when a marker having an imaging function and the drug are administered. If light is cast to the marker from outside the living body by using the light source, light having a wavelength of about 600 to 1500 nm is transmitted through the body and cast to the marker in the blood vessel since light having a wavelength of about 600 nm or shorter is absorbed by hemoglobin and light having a wavelength of about 1500 nm or longer is absorbed by water. Then, the marker having the imaging function emits the cast light as excitation light or absorbs a part of the light and reflects the remaining part of the light. Thus, light having a wavelength of about 700 to 1400 nm is emitted to outside of the living body.

Here, since light intensity generally increases as the concentration of the marker increases, transmission wavelength range of the variable-wavelength filter is changed and the photodetector unit detects intensity of light incident through the variable-wavelength filter and acquires intensity distribution (spectrum) of light emitted from plural positions on the measuring target. The drug concentration calculating unit holds, in advance, data on the correlation between light intensity distribution and marker concentration and the correlation between light intensity distribution and drug concentration. The drug concentration calculating unit calculates concentration of the drug administered with the marker in accordance with the light intensity distribution at the plural positions on the measuring target acquired by the photodetector unit. At this time, in this device, the drug concentration is calculated on the basis of the light intensity distribution in a predetermined wavelength range, for example, about 700 to 1400 nm, instead of calculating the drug concentration solely by using the intensity value of light having a specific wavelength. Therefore, the drug concentration can be accurately calculated. In this manner, with the in vivo drug concentration distribution measuring device according to this aspect of the invention, drug concentration distribution can be accurately and quickly measured by detecting emitted light from the living body, using a non-invasive technique without blood collection and so on.

According to another aspect of the invention, an in vivo drug concentration distribution measuring device includes: a light source which casts light to a living body as a measuring target; a variable-wavelength filter which, when the light is cast to the drug from outside of the living body, the light emitted from the drug to outside of the living body becomes incident on and transmits light of a predetermined wavelength range, of an entire wavelength range of the incident light, and which is capable of changing the predetermined wavelength range; a photodetector unit which detects intensity of light made incident through the variable-wavelength filter and acquires intensity distribution of light emitted from plural positions on the measuring target; and a drug concentration calculating unit which calculates a concentration of the drug in accordance with the intensity distribution of the light at the plural positions on the measuring target acquired by the photodetector unit.

The in vivo drug concentration distribution measuring device according to this aspect of the invention is a device which measures in vivo concentration distribution of a drug having an imaging function is administered. That is, if a drug having an imaging function can be administered to a living body, it is no longer necessary to use a marker having an imaging function. This in vivo drug concentration distribution measuring device can achieve effects and advantages similar to those described above and drug concentration distribution can be accurately and quickly measured by a non-invasive technique.

It is preferable that the variable-wavelength filter has plural sets of liquid crystal cells, each including a pair of polarizers, a liquid crystal layer inserted between the pair of polarizers, and an electrode which applies a voltage to the liquid crystal layer.

If a variable-wavelength filter having plural sets of liquid crystal cells is used, the transmission wavelength range can be optimized and the transmission wavelength range can easily be changed by adjusting the setting of the thickness of cell at the time of producing each liquid crystal cell and by adjusting the applied voltage at the time of use.

It is also preferable that an optical filter which interrupts light having a wavelength of 650 nm or shorter is provided on a light incident side of the photodetector unit.

With this configuration, light having a wavelength of 650 nm or shorter that is generated when using the variable-wavelength filter having liquid crystal cells can be interrupted. As noise components are eliminated, light intensity detection accuracy can be improved.

According to still another aspect of the invention, a variable-wavelength filter is used for a device which, when a marker having an imaging function and a drug or a drug having an imaging function is administered, measures in vivo concentration distribution of the drug. The variable-wavelength filter includes plural sets of liquid crystal cells, each having a pair of polarizers, a liquid crystal layer inserted between the pair of polarizers, and an electrode which applies a voltage to the liquid crystal layer. The pair of polarizers has transmission axes parallel to each other. The liquid crystal layer has liquid crystal molecules with homogeneous orientation. An angle formed by the transmission axes of the pair of polarizers and the direction of orientation of the liquid crystal molecules is $45°±5°$. The following formula (1) holds, where $\Delta n$ represents optical anisotropy of the liquid crystal layer with respect to light having a wavelength of 590 nm and d represents the thickness of the liquid crystal layer.

$$2^m(1.034 \times \Delta n^{-0.90}) < d < 2^m(2.266 \times \Delta n^{-0.82}) \qquad (1)$$

(m=0, 1, 2, 3, 4, 5)

With this configuration, the maximum wavelength of a peak value that can be detected by the variable-wavelength filter can be set within a range of 800 nm or longer and 1400 nm or shorter. Thus, a variable-wavelength filter suitable for the use of a marker that emits light having a wavelength of, for example, about 1100 nm, can be provided. The details of this variable-wavelength filter will be described later.

It is also preferable that the following formula (2) holds, where $\Delta n$ represents optical anisotropy of the liquid crystal layer with respect to light having a wavelength of 590 nm and d represents the thickness of the liquid crystal layer.

$$2^m(1.245 \times \Delta n^{-0.89}) < d < 2^m(1.865 \times \Delta n^{-0.83}) \qquad (2)$$

(m=0, 1, 2, 3, 4, 5)

With this configuration, the maximum wavelength of a peak value that can be detected by the variable-wavelength filter can be set within a range of 900 nm or longer and 1300 nm or shorter. Thus, a variable-wavelength filter suitable for the use of a marker that emits light having a wavelength of, for example, about 1100 nm, can be provided. The details of this variable-wavelength filter will be described later.

It is also preferable that the variable-wavelength filter includes a correction liquid crystal cell having a pair of polarizers, a liquid crystal layer inserted between the pair of polarizers, and an electrode which applies a voltage to the liquid crystal layer. The pair of polarizers has transmission axes orthogonal to each other. The liquid crystal layer has liquid crystal molecules with homogeneous orientation. An angle formed by the transmission axes of the pair of polarizers and the direction of orientation of the liquid crystal molecules is $45°±5°$.

With configuration, light that becomes a noise component can be eliminated by the correction liquid crystal cell.

According to still another aspect of the invention, an in vivo drug concentration distribution measuring method includes: administering a marker having an imaging function and a drug to a living body; casting light to the living body as a measuring target; when the light is cast to the marker from outside of the living body, detecting intensity of light of a predetermined wavelength range emitted from plural position on the measuring target, of the light emitted to outside of the living body from the marker, and repeating the detection of the intensity plural times while changing the predetermined wavelength range, thereby acquiring intensity distribution of the light emitted form the plural positions on the measuring target; and calculating a concentration of the drug administered with the marker in accordance with the intensity distribution of the light at the plural positions on the measuring target.

The in vivo drug concentration distribution measuring method according to this aspect of the invention is a method for administering both a marker having an imaging function and a drug to a living body, in the administration. In the in vivo drug concentration distribution measuring method according to this aspect of the invention, since drug concentration is calculated in accordance with intensity distribution of light having a predetermined wavelength range, the drug concentration can be accurately calculated. In this manner, with the in vivo drug concentration distribution measuring method according to this aspect of the invention, drug concentration distribution can be accurately and quickly measured by detecting emitted light from the living body, using a non-invasive technique without blood collection and so on.

It is preferable that, plural kinds of the markers are administered to the living body in the administration, then the intensity distribution of the light emitted from the plural positions on the measuring target is acquired for each of the plural kinds of the markers in the intensity distribution acquisition, and the concentration of the drug is calculated in accordance with the intensity distribution of the light at the plural positions on the measuring target corresponding to the plural kinds of the markers in the concentration calculation.

With this configuration, the concentration of the drug is calculated in accordance with the correlation between the concentration of the plural kinds of markers and the concentration of the drug. Therefore, the drug concentration can be calculated in a more practically manner.

According to still another aspect of the invention, an in vivo drug concentration distribution measuring method includes: administering a drug having an imaging function to a living body; casting light to the living body as a measuring target; when the light is cast to the drug from outside of the living body, detecting intensity of light of a predetermined wavelength range emitted from plural position on the measuring target, of the light emitted to outside of the living body from the drug, and repeating the detection of the intensity plural times while changing the wavelength range, thereby acquiring intensity distribution of the light emitted form the plural positions on the measuring target; and calculating a concentration of the drug in accordance with the intensity distribution of the light at the plural positions on the measuring target.

The in vivo drug concentration distribution measuring device according to this aspect of the invention is a method for administering a drug having an imaging function to a living body, in the administration. That is, if a drug having an imaging function can be administered to a living body, it is no longer necessary to use a marker having an imaging function. This in vivo drug concentration distribution measuring method can achieve effects and advantages similar to those described above and drug concentration distribution can be accurately and quickly measured by a non-invasive technique.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an embodiment of the invention will be described with reference to the drawings.

An in vivo drug concentration distribution measuring device according to this embodiment (hereinafter simply referred to as a "concentration distribution measuring device") is an exemplary device which measures in vivo concentration distribution of a drug where a marker having an imaging function and the drug are administered. A measuring target may be a human being or may be an animal such as rat or mouse frequently used for pharmacology tests. However, in this embodiment, it is assumed that the measuring target is a human being (patient).

Figure 1:
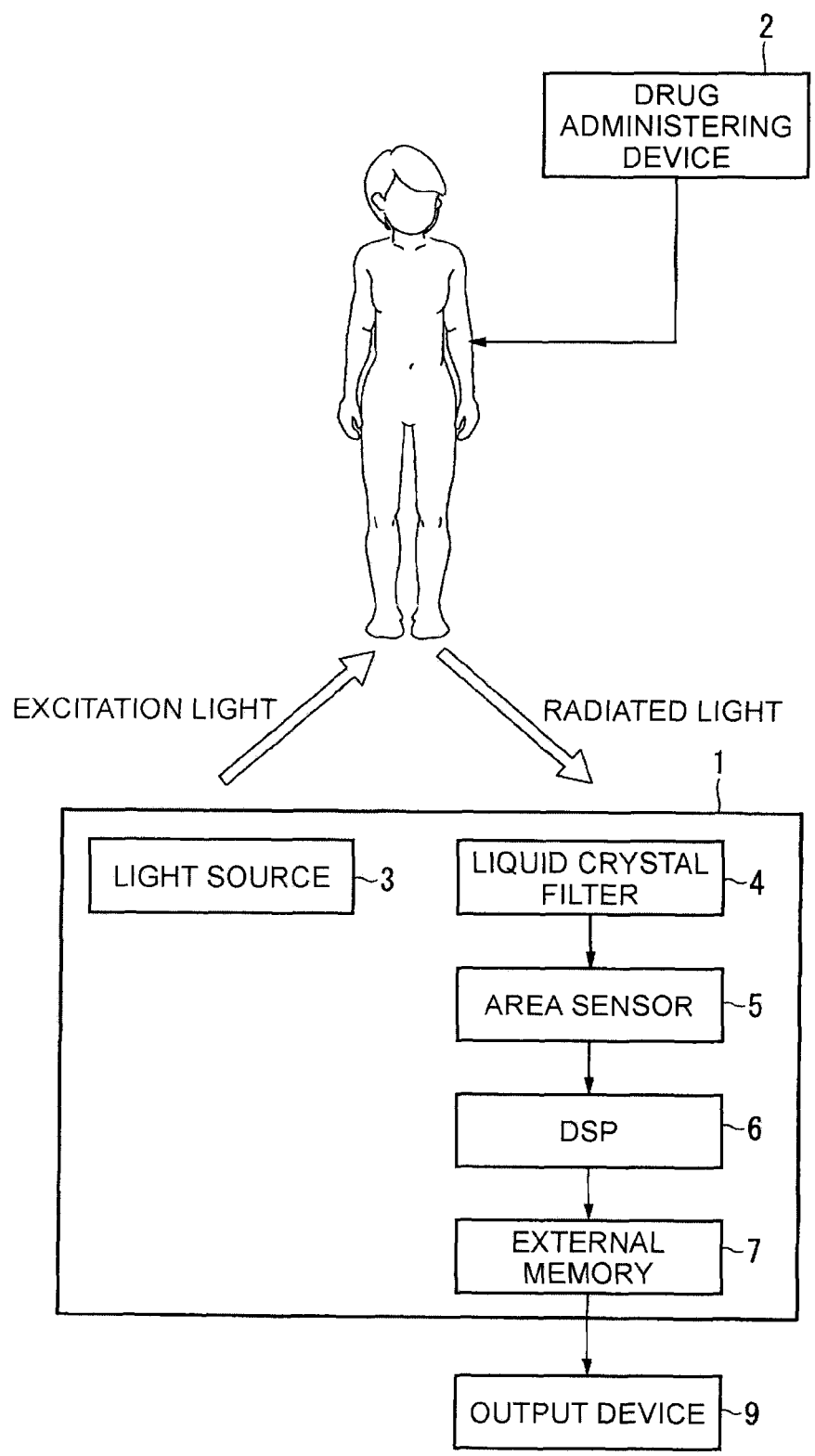
FIG. 1 is a block diagram showing a concentration distribution measuring device according to an embodiment of the invention.
Figure 2:
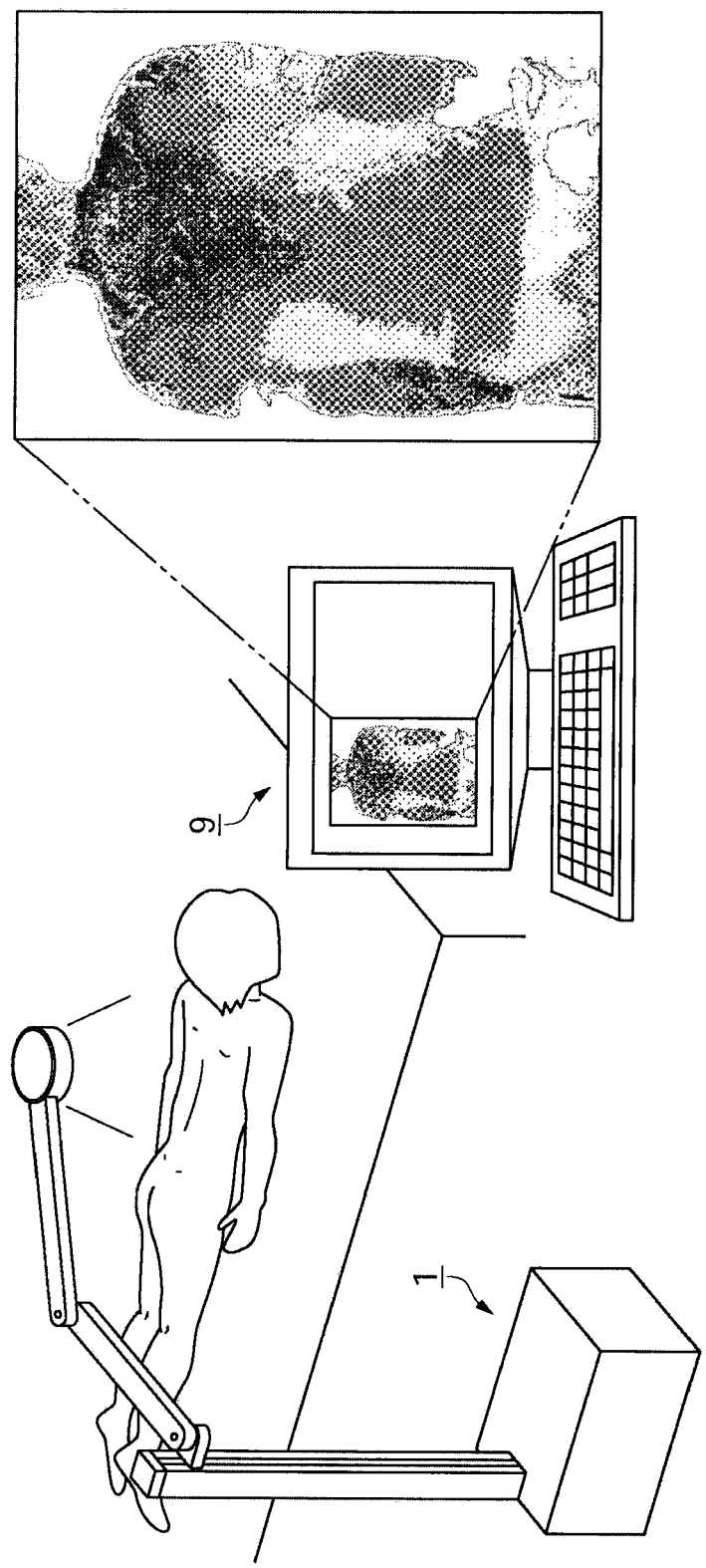
FIG. 2 is a perspective view showing an illustration of the state of use of the concentration distribution measuring device.

FIG. 1 is a block diagram showing a schematic configuration of the concentration distribution measuring device according to this embodiment. FIG. 2 is a perspective view showing an illustration of the state of use of the concentration distribution measuring device.

Configuration of Device

A concentration distribution measuring device 1 according to this embodiment has a light source 3, a liquid crystal filter 4 (variable-wavelength filter), an area sensor 5 (photodetector unit), a signal processor 6 (digital signal processor; DSP) (drug concentration calculating unit), and an external memory 7, as shown in FIG. 1. The light source 3 casts light (excitation light) to a living body as a measuring target. The liquid crystal filter 4 receives light emitted from a marker when light is cast to the marker in the living body and transmits light of a predetermined wavelength range, of the entire wavelength range of the incident light. The area sensor 5 detects the intensity of radiated light that is made incident via the liquid crystal filter 4. The DSP 6 calculates the concentration of the drug in accordance with the intensity distribution of the light at plural positions on the measuring target acquired by the area sensor 5. The external memory 7 stores image data acquired by the DSP 6.

Before measuring the concentration distribution of the drug, a mixture of a marker having an imaging function and a drug is administered to a human body using a drug administering device 2 (administration). To acquire in vivo information by using light, it is necessary to use light having a wavelength that is different from a wavelength absorbed by the components of the living body. Light having a wavelength of about 600 nm or shorter is absorbed by hemoglobin. Light having a wavelength of about 1500 nm or longer is absorbed by water. Therefore, light having these wavelengths cannot be used and light having a wavelength of about 600 to 1500 nm is transmitted through living tissue relatively well. In view of this, a marker having a characteristic of receiving light in a wavelength range of about 600 to 1500 nm and emitting the light of this wavelength range can be used for the concentration distribution measurement in this embodiment.

Specifically, as a marker, indocyanine green, gold nanorods, fluorescent contrast agent SF64 (trademark by Fuji Film) and so on can be used. Indocyanine green is a substance that is excited by irradiation with light having a wavelength of 750 to 780 nm and radiates near-infrared rays with a wavelength of approximately 800 to 1200 nm. Instead of indocyanine green, patent blue, indigo carmine or the like may be used. Gold nanorods refer rod-like nano-particles. Gold nanorods have high absorptivity in a near-infrared range and can be used as a contrast agent when near-infrared rays are used. The fluorescent contrast agent SF64 has a characteristic of generating intense fluorescent light in a near-infrared range.

Any invasive or non-invasive technique of administering the mixture of the marker and the drug may be used, including intradermal injection, subcutaneous injection, intramuscular injection, (peripheral infusion) intravenous injection, central venous injection, rectal administration, transdermal administration, pulmonary administration, nasal administration, and oral administration. More specifically, for example, in the case of intravenous injection using infusion, a drug administration micro-pump or the like that can adjust the dosage of the drug and the rate of application can be used.

As the light source 3, for example, a xenon lamp is used. From the light source 3 of the xenon lamp, light having a continuous spectrum from the visible range (blue range) to the infrared range is emitted and cast onto the human body as the measuring target (light irradiation). At this time, since the marker and the drug that are administered in advance are distributed in the human body, if light having a certain wavelength of the light from the light source 3 is transmitted through the human body and cast onto the marker, near-infrared rays are emitted from the marker. For example, if indocyanine green is used as the marker, the marker is excited by light having a wavelength of 750 to 780 nm of the light emitted from the light source 3 and radiates near-infrared rays having a wavelength of approximately 800 to 1200 nm in accordance with the concentration of the marker. Indocyanine has a characteristic of being excited by near-infrared rays and radiating near-infrared rays. However, the marker does not necessarily have to have a characteristic of radiating near-infrared rays and may have such a characteristic that absorption or reflection occurs in a quantity corresponding to the concentration of the marker and a predetermined quantity near-infrared rays are emitted.

The liquid crystal filter 4, the configuration of which will be described later in detail, includes plural sets of liquid crystal cells, each having a pair of substrates, a pair of polarizers arranged on the outer surface of the pair of substrates, a liquid crystal layer inserted between the pair of substrates, and a pair of electrodes which is arranged on the inner surface of the pair of substrates and applies a voltage to the liquid crystal layer. In the embodiment of the invention, the area sensor 5, which will be described later, needs to detect the light quantity with plural wavelengths and acquire the spectrum of radiated light, instead of detecting the light quantity with the wavelength at one point. Therefore, a variable-wavelength filter that can scan the transmission wavelength range on the light incident side of the area sensor 5 is necessary. The liquid crystal filter 4 functions as such a variable-wavelength filter. Several exemplary configurations of the liquid crystal filter 4 will be described later.

As the area sensor 5, a two-dimensional imaging sensor made up of a CCD or CMOS sensor is used. An imaging sensor of a CCD or CMOS sensor generally has a sensitivity area including near-infrared rays having a wavelength of approximately 800 to 1200 nm. Since light becomes incident on the area sensor 5 via the liquid crystal filter 4, the area sensor 5 only receives light in a predetermined wavelength range at a certain time point. However, the area sensor 5 can receive light in different wavelength ranges in accordance with the scanning of the transmission wavelength range of the liquid crystal filter 4 and can acquire the intensity distribution (spectrum) of light over the entire scanning time. The area sensor 5 transmits the intensity of the received near-infrared rays as an electric signal to the DSP 6, which will be described later. Although a two-dimensional imaging sensor is used in this example, a one-dimensional imaging sensor, that is, a so-called linear sensor, may also be used. In such a case, for example, a measuring area can be scanned by the linear sensor and the intensity of light in the two-dimensional measuring area can be detected.

Moreover, though not shown in FIG. 1, an optical filter which interrupts light that is not necessary for this concentration distribution measurement in the sensitivity area of the area sensor 5, for example, light having a wavelength of 700 nm or shorter, may be arranged to the light incident side of the area sensor 5. As an optical filter of this type, an ultraviolet and visible light cutting filter R-72 (trademark by Edmund) or the like can be used.

The DSP 6 receives the electric signal from the area sensor 5, then calculates the concentration of the marker based on the intensity distribution of light at each point on the measuring target, and calculates the concentration of the drug from the concentration of the marker. In this manner, as the concentration of the drug at each point on the measuring target is calculated, the in vivo drug concentration distribution can be learned as a whole. The acquired measurement data of the drug concentration distribution is sent from the DSP 6 to an arbitrary output device 9 such as a liquid crystal monitor, where the magnitude of the drug concentration is expressed with colors and density of the colors so that users such as physicians and nurses can visually confirm the drug concentration, as shown in FIG. 2.

Liquid Crystal Filter-1

Now, a first exemplary configuration of the liquid crystal filter 4 will be described with reference to FIG. 3 to FIG. 6.

Figure 3:
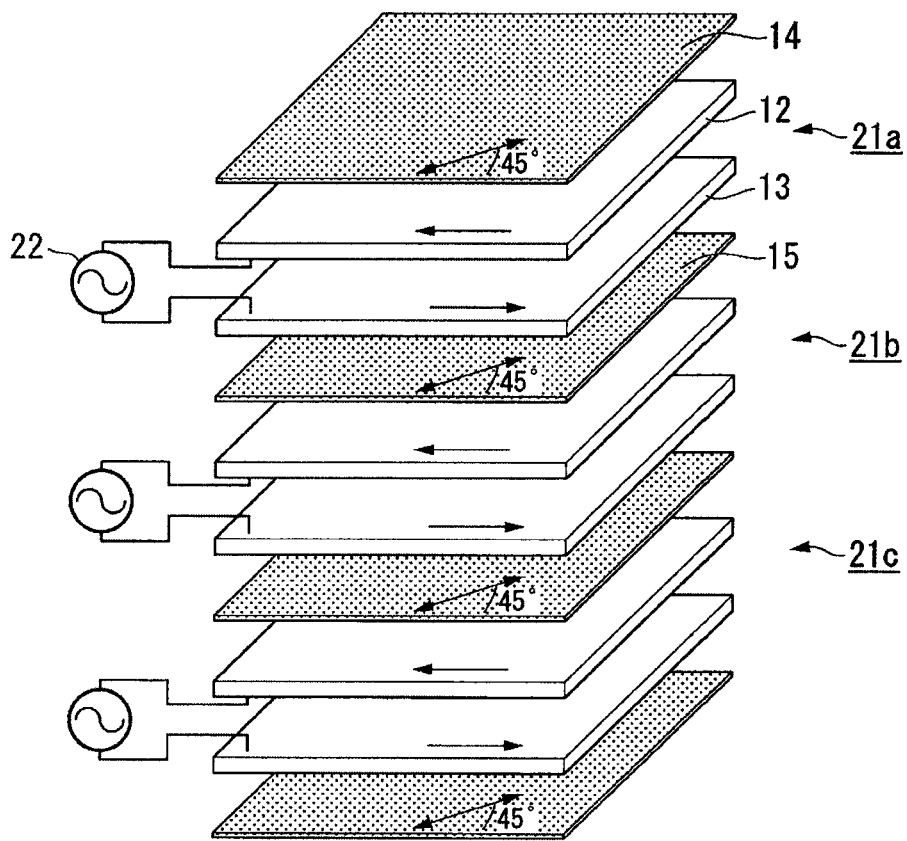
FIG. 3 is a perspective view showing a liquid crystal filter of a first exemplary configuration, in an exploded view.
Figure 4:
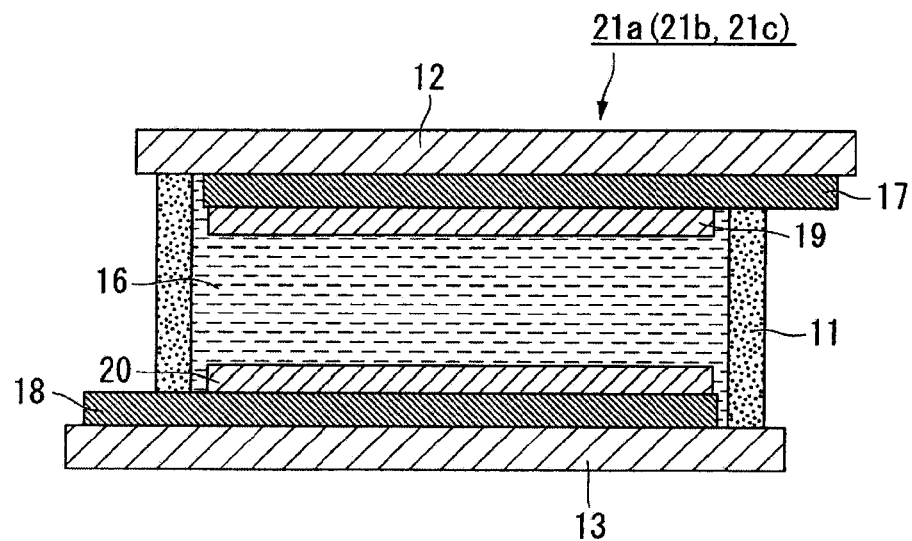
FIG. 4 is a sectional view showing one liquid crystal cell constituting the liquid crystal filter.
Figure 5:
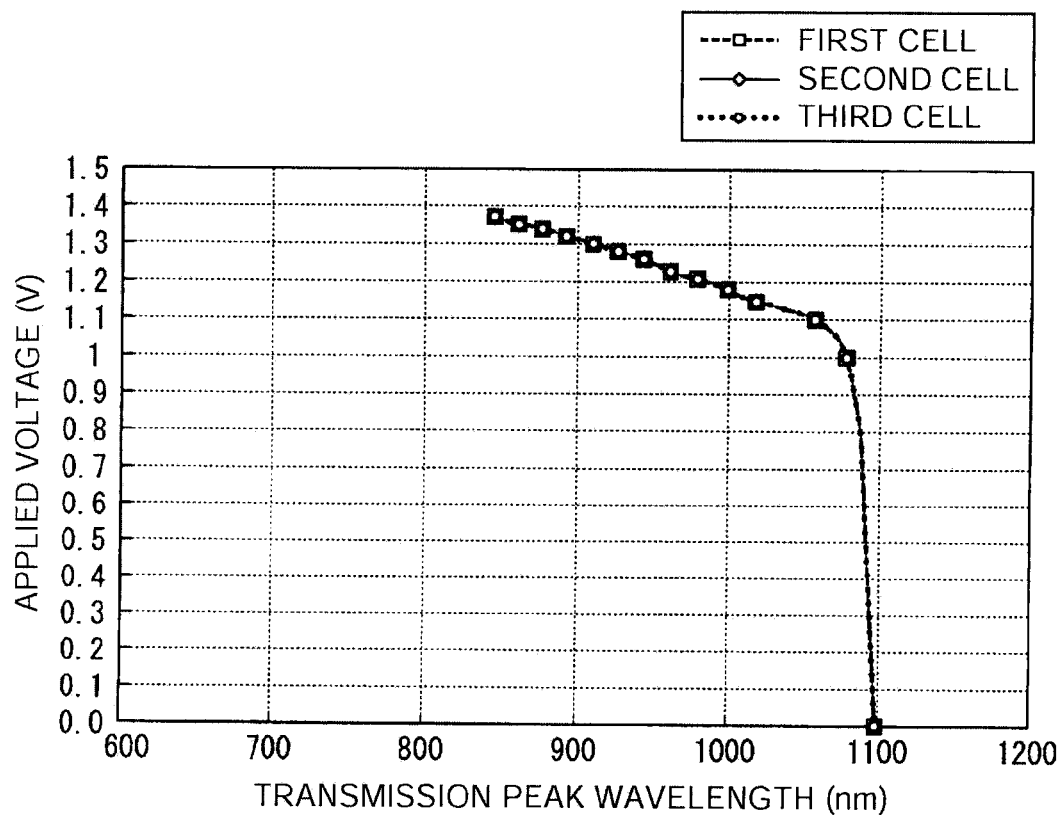
FIG. 5 is a graph showing the relation between applied voltage to each liquid crystal cell and transmission peak wavelength.
Figure 6:
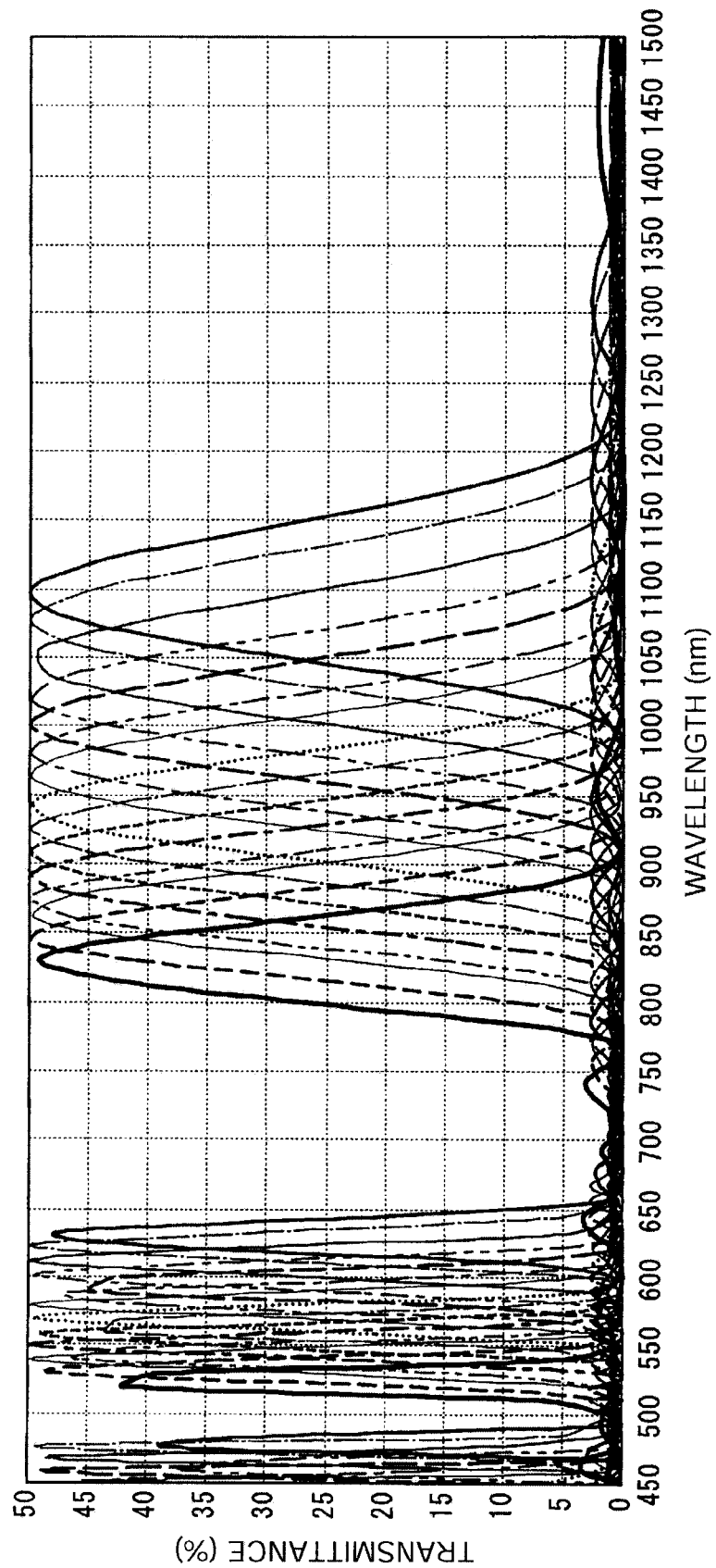
FIG. 6 shows spectroscopic properties of the liquid crystal filter.

FIG. 3 is a perspective view showing the liquid crystal filter 4 of this exemplary configuration, in an exploded view. FIG. 4 is a sectional view showing one liquid crystal cell constituting the liquid crystal filter 4. FIG. 5 is a graph showing the relation between applied voltage to each liquid crystal cell and transmission peak wavelength. FIG. 6 shows spectroscopic properties of the liquid crystal filter.

Specific numeric values of applied voltage to a liquid crystal cell, transmission wavelength and so on which are described below are based on the result of simulation carried out by the inventors.

The liquid crystal filter 4 of this exemplary configuration includes three sets of liquid crystal cells 21a, 21b and 21c stacked on each other, each having a pair of glass substrates 12 and 13 bonded to each other via a sealant 11, a pair of polarizers 14 and 15 arranged on the outer surface of the pair of glass substrates 12 and 13, a liquid crystal layer 16 inserted between the pair of glass substrates 12 and 13, a pair of electrodes 17 and 18 which is arranged on the inner surface of the pair of glass substrates 12 and 13 and applies a voltage to the liquid crystal layer 16, and oriented films 19 and 20 on the electrodes 17 and 18, as shown in FIG. 3 and FIG. 4. However, as the polarizer located between the neighboring sets of liquid crystal cells, one polarizer is shared by the two liquid crystal cells. In the following description, for convenience, the liquid crystal cells are referred to as "the first liquid crystal cell 21a", "the second liquid crystal cell 21b" and "the third liquid crystal cell 21c" and so on, from top to bottom in the drawings.

In the first to third liquid crystal cells 21a, 21b and 21c, the pair of glass substrates 12 and 13 is in the state of so-called antiparallel orientation, where the pair of glass substrates 12 and 13 has directions of orientation that are parallel and opposite to each other. Thus, liquid crystal molecules constituting the liquid crystal layer 16 in the liquid crystal cells 21a, 21b and 21c are in the state of homogeneous orientation. The pair of polarizers 14 and 15, which are arranged with the pair of glass substrates 12 and 13 held between the polarizers, have parallel transmission axes to each other and the direction of the transmission axes is arranged to form an angle of 45°±5° with the direction of orientation of one substrate. As the polarizers 14 and 15, iodine-containing polarization films do not have a polarizing property in the near-infrared range and therefore are not preferable. It is preferable to use multi-layer reflection polarizers having alternately stacked retardation layers and isotropic layers, or wire-grid reflection polarizers. Between the pair of electrodes 17 and 18 of the liquid crystal cells 21a, 21b and 21c, a driving circuit 22 for applying a voltage to the pair of electrodes 17 and 18 is connected.

In all the first to third liquid crystal cells 21a, 21b and 21c, the value of optical anisotropy $\Delta n$ of the liquid crystal layer 16 of each liquid crystal cell with respect to light having a wavelength of 590 nm is set to 0.201. Meanwhile, the thickness of the liquid crystal layer 16 (the cell gap between the pair of substrates 12 and 13) is different among the first to third liquid crystal cells 21a, 21b and 21c. The thickness of the liquid crystal layer in the first liquid crystal cell 21a is 6.5 μm. The thickness of the liquid crystal layer in the second liquid crystal cell 21b is 12.9 μm. The thickness of the liquid crystal layer in the third liquid crystal cell 21c is 25.8 μm. In the liquid crystal filter 4 of this exemplary configuration, a spectrum having 15 stages in a wavelength range of 830 to 1098 nm is selected. Therefore, the DSP 6 controls the driving circuit 22 to supply one of 15 stages of applied voltages to the liquid crystal cells 21a, 21b and 21c of the liquid crystal filter 4. The DSP 6 applies substantially the same voltage to the first to third liquid crystal cells 21a, 21b and 21c. However, the voltage is slightly corrected with reference to correction data that is stored in advance in a memory.

In taking in the intensity of light radiated from the measuring target as image data, first, the applied voltage to the first to third liquid crystal cells 21a, 21b and 21c is 0 V. Then, the liquid crystal filter 4 shows a transmission property having a peak at 1098 nm. The liquid crystal filter 4 transmits light having a wavelength of 1098 nm and this light becomes incident on an array-like pixel surface of the area sensor 5. Here, the area sensor 5 sequentially detects the intensity of the incident light for each pixel, reads out the entire image equivalent to one screen at 30 msec, converts the image to an electric signal, and then outputs the electric signal to the DSP 6. The DSP 6 stores the image data equivalent to one screen at the wavelength of 1098 nm, in the external memory 7. Thus, a first cycle of selected image data intake is finished.

Next, the applied voltage to the first to third liquid crystal cells 21a, 21b and 21c is turned to 1.0 V. Then, the liquid crystal filter 4 shows a transmission property having a peak at 1077 nm. Light having a wavelength of 1077 nm becomes incident on the area sensor 5. The area sensor 5 reads out an image equivalent to one screen at 30 msec, converts the image to an electric signal, and then outputs the electric signal to the DSP 6. The DSP 6 stores the image data equivalent to one screen at the wavelength of 1077 nm, in the external memory 7. Thus, a second cycle of selected image data intake is finished.

In third and subsequent cycles, the applied voltage to the first to third liquid crystal cells 21a, 21b and 21c is changed to 1.10 V, 1.15 V, 1.18 V, 1.21 V, 1.23 V, 1.26 V, 1.28 V, 1.30 V, 1.32 V, 1.34 V, 1.35 V, 1.37 V, and 1.39 V (in the final cycle, the applied voltage is corrected to 1.42 V only for the liquid crystal cell 21a), as shown in TABLE 1. Then, in accordance with the changes in voltage, the transmission peak wavelength changes to 1057 nm, 1018 nm, 999 nm, 980 nm, 962 nm, 944 nm, 927 nm, 910 nm, 893 nm, 877 nm, 861 nm, 845 nm, and 830 nm. Thus, all the 15 cycles of selected image data intake are finished (acquisition of intensity distribution).

TABLE 1

| | TRANSMISSION PEAK WAVELENGTH (nm) | | | | | | | | | | | | | | |
|---|---|---|---|---|---|---|---|---|---|---|---|---|---|---|---|
| | 1098 | 1077 | 1057 | 1018 | 999 | 980 | 944 | 944 | 927 | 910 | 893 | 877 | 861 | 845 | 830 |
| APPLIED VOLTAGE (V) TO FIRST CELL | 0 | 1.00 | 1.10 | 1.15 | 1.18 | 1.21 | 1.23 | 1.26 | 1.28 | 1.30 | 1.32 | 1.34 | 1.35 | 1.37 | 1.42 |
| APPLIED VOLTAGE (V) TO SECOND CELL | 0 | 1.00 | 1.10 | 1.15 | 1.18 | 1.21 | 1.23 | 1.26 | 1.28 | 1.30 | 1.32 | 1.34 | 1.35 | 1.37 | 1.39 |
| APPLIED VOLTAGE (V) TO THIRD CELL | 0 | 1.00 | 1.10 | 1.15 | 1.18 | 1.21 | 1.23 | 1.26 | 1.28 | 1.30 | 1.32 | 1.34 | 1.35 | 1.37 | 1.39 |

FIG. 5 is a graph showing the data of TABLE 1. That is, FIG. 5 is a graph showing the relation between applied voltage to the liquid crystal cells 21a, 21b and 21c and transmission peak wavelength. The vertical axis represents applied voltage (V) and the horizontal axis represents transmission peak wavelength (nm). FIG. 6 shows spectroscopic properties of the liquid crystal filter 4 based on the values of transmission peak wavelength. That is, with this exemplary configuration, a liquid crystal filter having the spectroscopic properties shown in FIG. 6 and having a transmission wavelength range of 800 to 1100 nm can be realized. In the spectrum shown in FIG. 6, wavelength components of 700 nm and shorter are noise components that are unnecessary for this concentration distribution measurement. Therefore, it is desirable to eliminate these noise components by using the above optical filter.

Liquid Crystal Filter-2

A second exemplary configuration of the liquid crystal filter 4 will be described with reference to FIG. 7 and FIG. 8.

Figure 7:
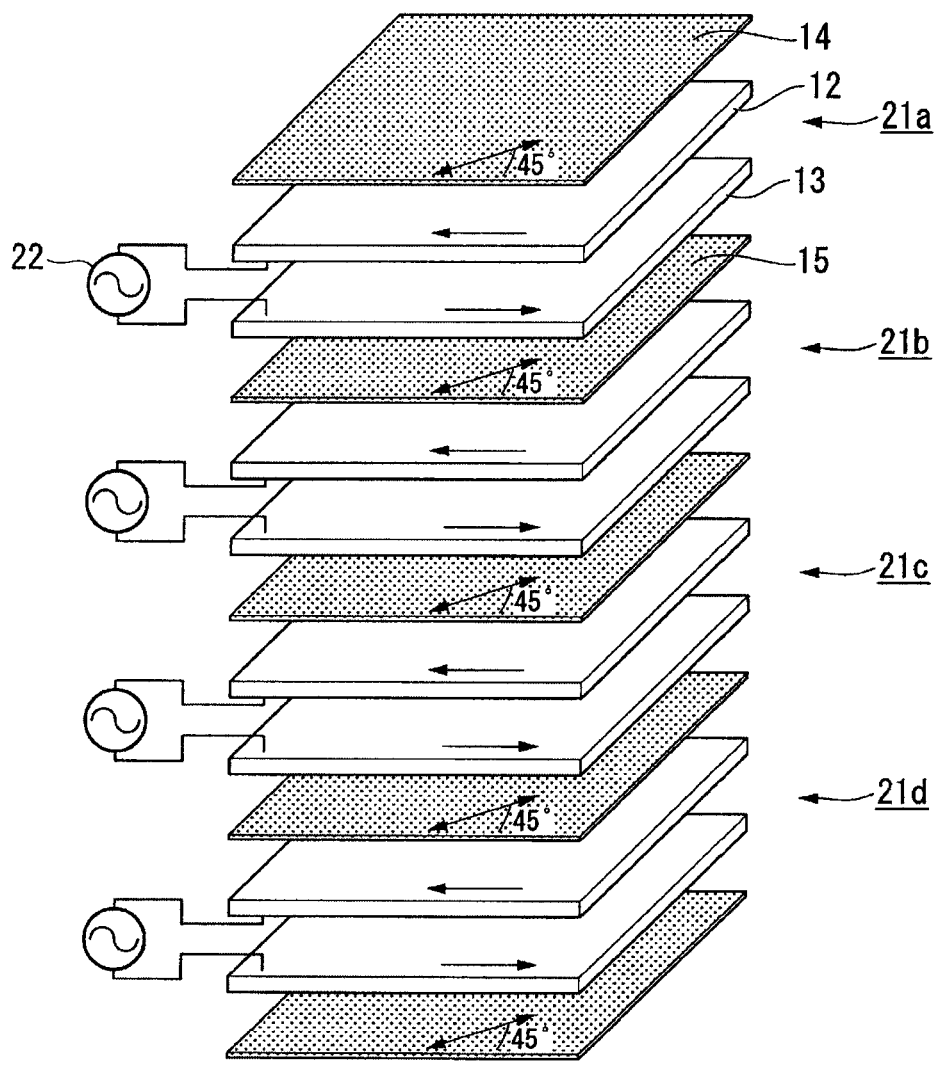
FIG. 7 is a perspective view showing a liquid crystal filter of a second exemplary configuration, in an exploded view.

FIG. 7 is a perspective view showing the liquid crystal filter of this exemplary configuration, in an exploded view. FIG. 8 shows spectroscopic properties of the liquid crystal filter. In FIG. 7, the same components as those in the first exemplary configuration shown in FIG. 3 are denoted by the same reference numerals and will not be described further in detail.

This exemplary configuration is different from the first exemplary configuration in that while the liquid crystal filter of the first exemplary configuration includes the three sets of liquid crystal cells 21a, 21b and 21c stacked on each other, the liquid crystal filter of this exemplary configuration includes four sets of liquid crystal cells 21a, 21b, 21c and 21d stacked on each other. In the liquid crystal filter of this exemplary configuration, the fourth liquid crystal cell 21d is stacked below the third liquid crystal cell 21c, as shown in FIG. 7. The fourth liquid crystal cell 21d has the same direction of orientation and the same direction of transmission axis of the polarizer as the first to third liquid crystal cells 21a, 21b and 21c. However, the thickness of the liquid crystal layer is different. The thickness of the liquid crystal layer in the first liquid crystal cell 21a is 6.5 µm. The thickness of the liquid crystal layer in the second liquid crystal cell 21b is 12.9 µm. The thickness of the liquid crystal layer in the third liquid crystal cell 21c is 25.8 µm. The thickness of the liquid crystal layer in the fourth liquid crystal cell 21d is 51.6 µm.

The relation between applied voltage to the liquid crystal cells 21a, 21b, 21c and 21d and transmission peak wavelength is as shown in TABLE 2. The applied voltages to the first to third liquid crystal cells 21a, 21b and 21c are the same. The applied voltage to the fourth liquid crystal cell 21d is substantially the same as the applied voltage to the first to third liquid crystal cells 21a, 21b and 21c but is slightly adjusted.

TABLE 2

| | TRANSMISSION PEAK WAVELENGTH (nm) | | | | | | |
|---|---|---|---|---|---|---|---|
| | 1100 | 1050 | 1000 | 950 | 900 | 850 | 800 |
| APPLIED VOLTAGE (V) TO FIRST TO THIRD CELLS | 0 | 1.10 | 1.18 | 1.25 | 1.31 | 1.37 | 1.43 |

Figure 8:
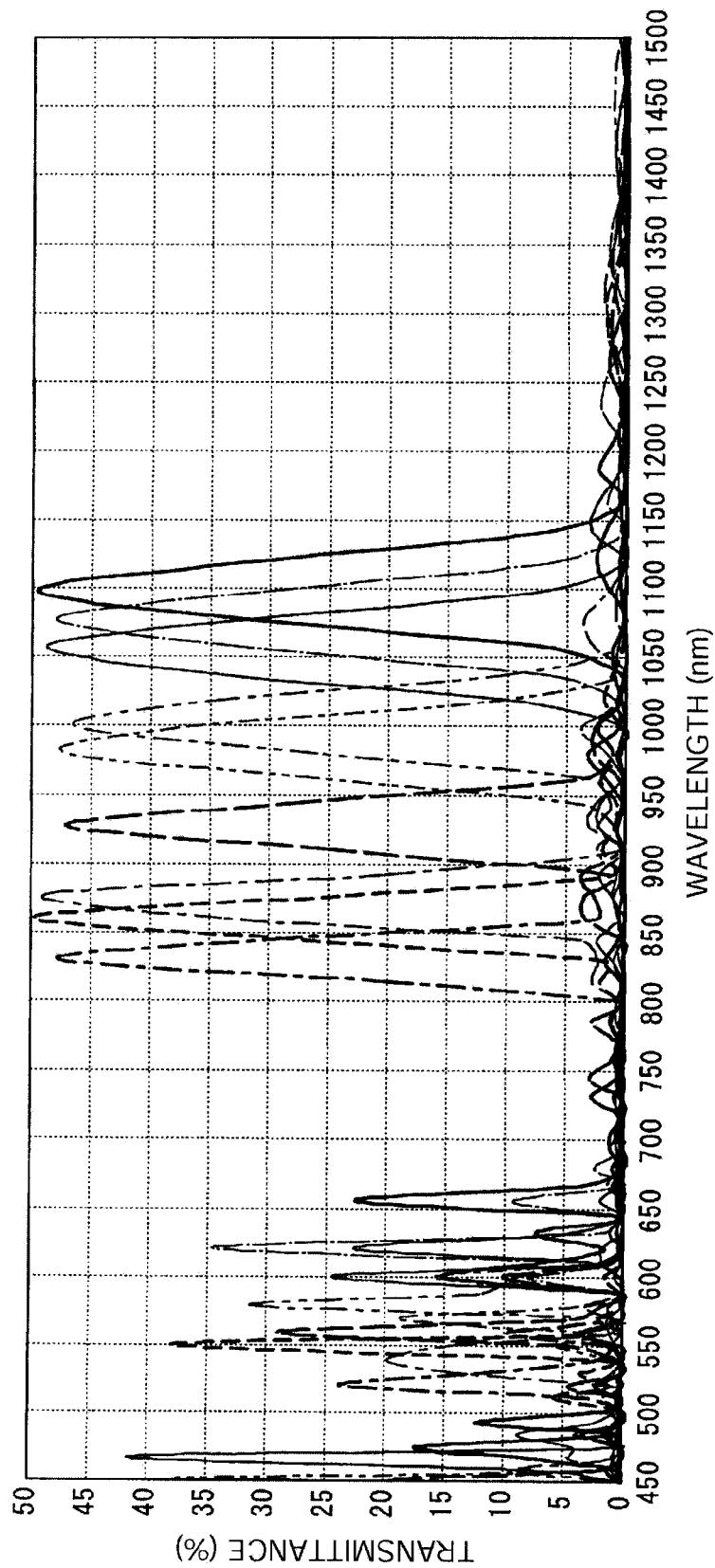
FIG. 8 shows spectroscopic properties of the liquid crystal filter.

FIG. 8 shows spectroscopic properties of the liquid crystal filter 4 based on the values of transmission peak wavelength shown in TABLE 2. With this exemplary configuration, a variable-wavelength filter having the spectroscopic properties shown in FIG. 8 and having a transmission wavelength range of 800 to 1100 nm can be realized. Compared with the first exemplary configuration, four layers of liquid crystal cells are used instead of three layers. Therefore, the half width of the transmission wavelength range, which is as broad as 70 to 90 nm in the first exemplary configuration, is narrowed to 30 to 50 nm in this exemplary configuration. Thus, detection accuracy of the marker concentration can be improved.

Liquid Crystal Filter-3

A third exemplary configuration of the liquid crystal filter will be described.

The liquid crystal filter of this exemplary configuration has four sets of liquid crystal cells stacked on each other, as in the liquid crystal filter of the second exemplary configuration. The direction of orientation of each liquid crystal cell and the direction of transmission axis of the polarizer are the same as in the second exemplary configuration. However, the thickness of the liquid crystal layer is different. The thickness of the liquid crystal layer in the first liquid crystal cell is 6.5 µm. The thickness of the liquid crystal layer in the second liquid crystal cell is 12.9 µm. The thickness of the liquid crystal layer in the third liquid crystal cell is 51.6 µm. The thickness of the liquid crystal layer in the fourth liquid crystal cell is 51.6 µm. That is, in this exemplary configuration, the same liquid crystal cell as the fourth liquid crystal cell is used as the third liquid crystal cell.

The relation between applied voltage to each liquid crystal cell and transmission peak wavelength is as shown in TABLE 3. The same voltage is applied to the first and second liquid crystal cells. A higher voltage than the applied voltage to the first and second liquid crystal cells is applied to the third liquid crystal cell. The applied voltage to the fourth liquid crystal cell is substantially the same as the applied voltage to the first and second liquid crystal cells but is slightly adjusted.

TABLE 3

| | TRANSMISSION PEAK WAVELENGTH (nm) | | | | | | |
|---|---|---|---|---|---|---|---|
| | 1100 | 1050 | 1000 | 950 | 900 | 850 | 800 |
| APPLIED VOLTAGE (V) TO FIRST AND SECOND CELLS | 0 | 1.11 | 1.22 | 1.26 | 1.31 | 1.37 | 1.43 |
| APPLIED VOLTAGE (V) TO THIRD CELL | 1.85 | 2.02 | 2.05 | 2.07 | 2.10 | 2.12 | 2.15 |

Although not shown in the drawings, also with this exemplary configuration, a variable-wavelength filter having substantially the same spectroscopic properties as the liquid crystal filter of the second exemplary configuration can be realized. In this exemplary configuration, unlike the second exemplary configuration, the third liquid crystal cell having the same specifications as the fourth liquid crystal cell can be used. Therefore, there is an advantage that the liquid crystal filter can be manufactured more easily.

Liquid Crystal Filter-4

A fourth exemplary configuration of the liquid crystal filter will be described.

The liquid crystal filter of this exemplary configuration has four sets of liquid crystal cells stacked on each other, as in the liquid crystal filters of the second and third exemplary configurations. The direction of orientation of each liquid crystal cell and the direction of transmission axis of the polarizer are the same as in the second and third exemplary configurations. However, the thickness of the liquid crystal layer is different. The thickness of the liquid crystal layer in the first liquid crystal cell is 12.9 µm. The thickness of the liquid crystal layer in the second liquid crystal cell is 12.9 µm. The thickness of the liquid crystal layer in the third liquid crystal cell is 51.6 µm. The thickness of the liquid crystal layer in the fourth liquid crystal cell is 51.6 µm. That is, the same liquid crystal cell as the second liquid crystal cell is used as the first liquid crystal cell, and the same liquid crystal cell as the fourth liquid crystal cell is used as the third liquid crystal cell.

The relation between applied voltage to each liquid crystal cell and transmission peak wavelength is as shown in TABLE 4. A higher voltage than the applied voltage to the second liquid crystal cell is applied to the first liquid crystal cell. The applied voltage to the third liquid crystal cell is substantially the same as the applied voltage to the first liquid crystal cell, and the applied voltage to the fourth liquid crystal cell is substantially the same as the applied voltage to the second liquid crystal cell, but both are slightly adjusted.

TABLE 4

| | TRANSMISSION PEAK WAVELENGTH (nm) | | | | | | |
|---|---|---|---|---|---|---|---|
| | 1100 | 1050 | 1000 | 950 | 900 | 850 | 800 |
| APPLIED VOLTAGE (V) TO FIRST CELL | 1.95 | 2.00 | 2.04 | 2.11 | 2.15 | 2.18 | 2.22 |
| APPLIED VOLTAGE (V) TO SECOND CELL | 0 | 1.11 | 1.23 | 1.28 | 2.33 | 1.37 | 1.43 |

Although not shown in the drawings, also with this exemplary configuration, a variable-wavelength filter having substantially the same spectroscopic properties as the liquid crystal filters of the second and third exemplary configurations can be realized. In this exemplary configuration, the first liquid crystal cell having the same specifications as the second liquid crystal cell can be used and the third liquid crystal cell having the same specifications as the fourth liquid crystal cell can be used. Therefore, there is an advantage that the liquid crystal filter can be manufactured more easily than in the case of the third exemplary configuration.

Liquid Crystal Filter-5

A fifth exemplary configuration of the liquid crystal filter will be described.

In the first to fourth exemplary configurations, the value of optical anisotropy Δn of each liquid crystal cell with respect to light having a wavelength of 590 nm is set to 0.201. However, in this exemplary configuration, the value of optical anisotropy Δn of each liquid crystal cell with respect to light having a wavelength of 590 nm is set to 0.136. As the value of optical anisotropy Δn is changed, the thickness of the liquid crystal layer in the first liquid crystal cell is changed to 9.0 μm. The thickness of the liquid crystal layer in the second liquid crystal cell is changed to 18.0 μm. The thickness of the liquid crystal layer in the third liquid crystal cell is changed to 36.1 μm. The thickness of the liquid crystal layer in the fourth liquid crystal cell is changed to 72.1 μm.

Although not shown in the drawings, also with this exemplary configuration, a variable-wavelength filter having substantially the same spectroscopic properties as the liquid crystal filters of the second to fourth exemplary configurations can be realized. That is, it is found that even when the value of optical anisotropy Δn of the liquid crystal layer is changed, a preferable variable-wavelength filter for the invention can be provided if the thickness d of the liquid crystal layer is properly set according to the value of optical anisotropy.

Relation Between Δn and d in Liquid Crystal Filter

Next, spectroscopic properties are examined where the optical anisotropy Δn of the liquid crystal cell with respect to light having a wavelength of 590 nm (hereinafter referred to as Δn (590 nm)) and the thickness d of the liquid crystal layer are changed. The results will now be explained.

Here, the thickness dm of the liquid crystal layer of an m-th liquid crystal cell satisfies the relation of $dm=2^m \times d0$, where d0 represents the thickness of the liquid crystal layer of the first liquid crystal cell.

Figure 9:
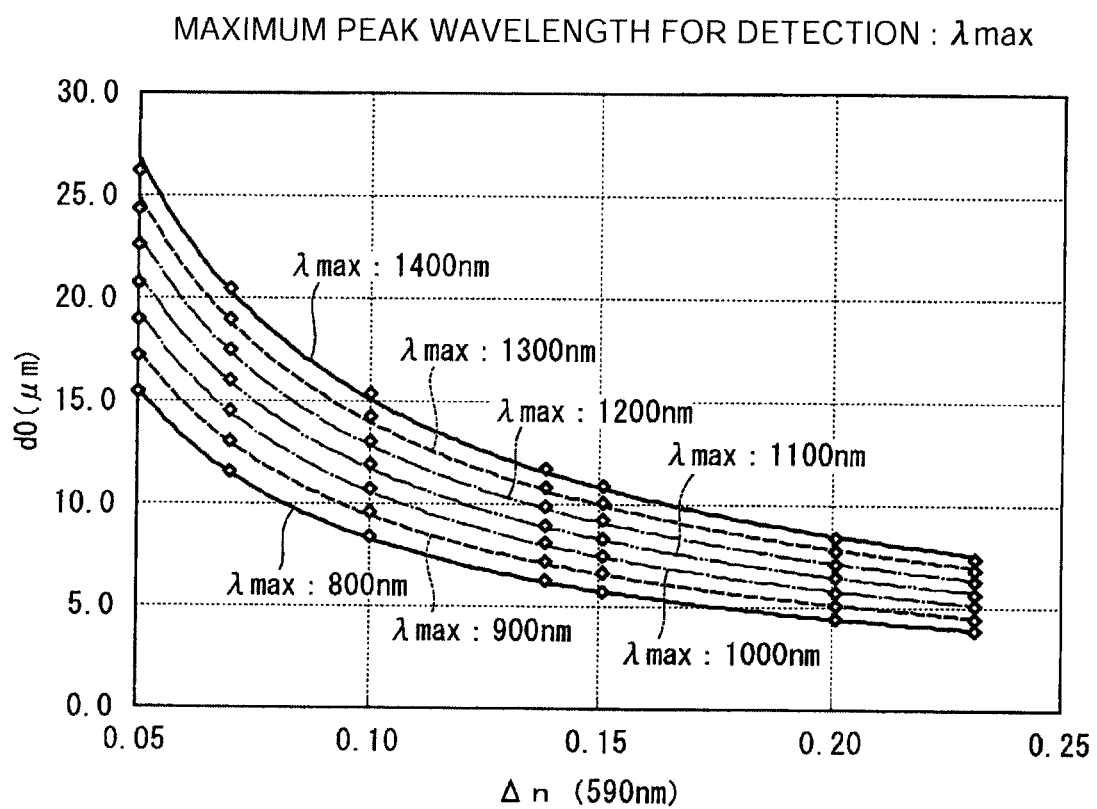
FIG. 9 is a graph showing the relation between optical anisotropy $\Delta n$ and thickness of liquid crystal $d0$ of a first liquid crystal cell, for each maximum value of transmission peak wavelength of the liquid crystal filter.

The optical anisotropy Δn (590 nm) of the liquid crystal cell and the thickness d of the liquid crystal layer are changed to various values and a maximum value λmax of transmission peak wavelength of the liquid crystal filter is found. FIG. 9 shows the relation between the optical anisotropy Δn (590 nm) and the thickness d0 of the first liquid crystal cell for each maximum value λmax of transmission peak wavelength of the liquid crystal filter. The horizontal axis in FIG. 9 represents the optical anisotropy Δn (590 nm) [nm], and the vertical axis represents the thickness d0 [μm] of the first liquid crystal cell.

If the maximum value λmax of transmission peak wavelength of the liquid crystal filter is 800 nm or smaller, near-infrared rays radiated from the marker cannot be transmitted through the liquid crystal filter and it is difficult to detect the concentration of the marker. Therefore, the lower limit of the maximum value λmax is 800 nm. If a relational expression between Δn (590 nm) and the thickness d of the liquid crystal layer is found from the relation between Δn (590 nm) and d0 on the curve having λmax of 800 nm shown in FIG. 9, the following equation (3) holds.

$$d=2^m(1.034\times\Delta n^{-0.90}) \qquad (3)$$

(m=0, 1, 2, 3, 4, 5)

However, the optimum thickness of the liquid crystal layer needs to be greater than d expressed by the equation (3).

Meanwhile, if the maximum value λmax of transmission peak wavelength of the liquid crystal filter is 1400 nm or greater, a high voltage of 2 to 3 V needs to be applied in order to detect near-infrared rays having a wavelength of 1200 nm or shorter and the spectroscopic properties become unstable. Therefore, the upper limit of the maximum value λmax is 1400 nm. If a relational expression between Δn (590 nm) and the thickness d of the liquid crystal layer is found from the relation between Δn (590 nm) and d0 on the curve having λmax of 1400 nm shown in FIG. 9, the following equation (4) holds.

$$d=2^m(2.266\times\Delta n^{-0.82}) \qquad (4)$$

(m=0, 1, 2, 3, 4, 5)

However, the optimum thickness of the liquid crystal layer needs to be smaller than d expressed by the equation (4).

Therefore, in accordance with the equations (3) and (4), the optimum thickness d of the liquid crystal layer is expressed as follows.

$$2^m(1.034\times\Delta n^{-0.90})<d<2^m(2.266\times\Delta n^{-0.82}) \qquad (5)$$

(m=0, 1, 2, 3, 4, 5)

Basically, it suffices to satisfy the formula (5). However, if more desirable conditions are sought, the following is found.

If the maximum value λmax of transmission peak wavelength of the liquid crystal filter is 900 nm or greater, noise components of near-infrared rays radiated from the marker can be eliminated and intensity can be detected more easily. Thus, if the optical thickness d of the liquid crystal layer is found according to the above procedure by using the curve having λmax of 900 nm shown in FIG. 9, the following equation (6) holds.

$$d=2^m(1.245\times\Delta n^{-0.89}) \qquad (6)$$

(m=0, 1, 2, 3, 4, 5)

However, the optimum thickness of the liquid crystal layer needs to be greater than d expressed by the equation (6).

Meanwhile, if the maximum value λmax of transmission peak wavelength of the liquid crystal filter is 1300 nm or smaller, near-infrared rays having a wavelength of 1200 nm or shorter can be detected more stably without applying a high voltage. Thus, if the optical thickness d of the liquid crystal layer is found according to the above procedure by using the curve having λmax of 1300 nm shown in FIG. 9, the following equation (7) holds.

$$d=2^m(1.865\times\Delta n^{-0.83}) \qquad (7)$$

(m=0, 1, 2, 3, 4, 5)

However, the optimum thickness of the liquid crystal layer needs to be smaller than d expressed by the equation (7).

Therefore, in accordance with the equations (6) and (7), the optimum thickness d of the liquid crystal layer is expressed as follows.

$$2^m(1.245 \times \Delta n^{-0.89}) < d < 2^m(1.865 \times \Delta n^{-0.83}) \quad (8)$$

(m=0, 1, 2, 3, 4, 5)

It is preferable that the value "m" in the formulas is one of 0, 1, 2, 3, 4 and 5. On the basis of such a numeric range of "m", the numeric range of the thickness d of the liquid crystal layer in the above formulas can be approximately several μm to 100 μm. This numeric range is preferable because if the value of "m" exceeds 5, inconvenience occurs including the facts that the transmission wavelength range as a band-pass filter is too small, that the transmittance starts to be lowered, and that the thickness d of the liquid crystal layer becomes 100 μm or greater and it is difficult to produce liquid crystal cells.

Liquid Crystal Filter-6

A sixth exemplary configuration of the liquid crystal filter will be described with reference to FIG. 10 to FIG. 12.

Figure 10:
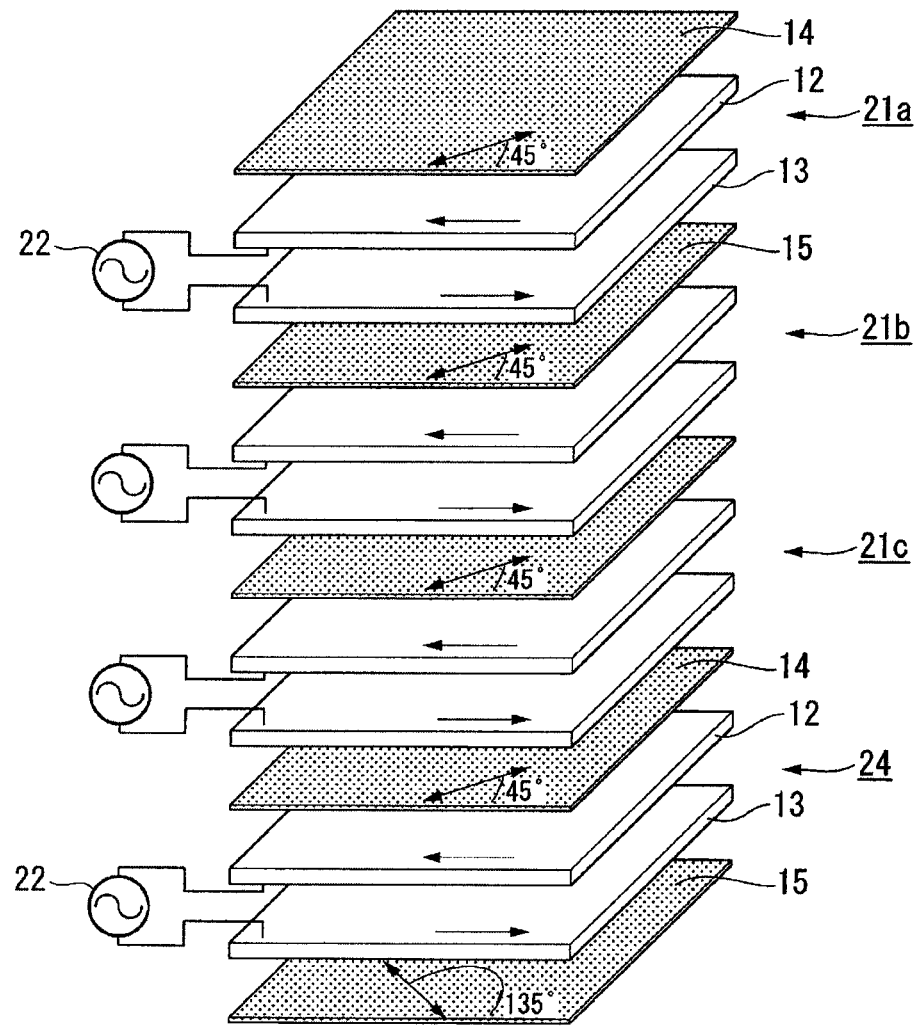
FIG. 10 is a perspective view showing a liquid crystal filter of a sixth exemplary configuration, in an exploded view.
Figure 11:
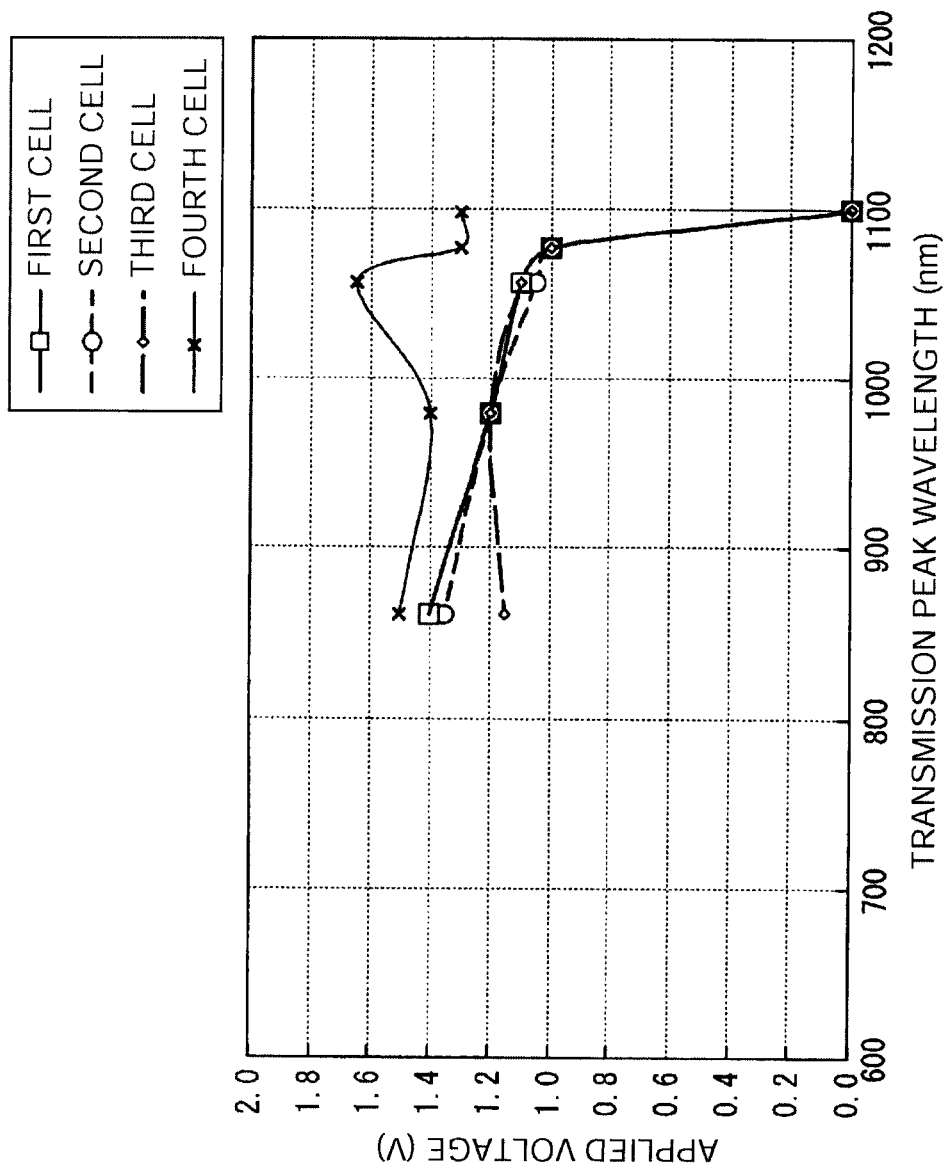
FIG. 11 is a graph showing the relation between applied voltage to each liquid crystal cell and transmission peak wavelength.

FIG. 10 is a perspective view showing the liquid crystal filter of the sixth exemplary configuration, in an exploded view. FIG. 11 is a graph showing the relation between applied voltage to each liquid crystal cell and transmission peak wavelength. FIG. 12 shows spectroscopic properties of the liquid crystal filter. In FIG. 10, the same components as in the first exemplary configuration shown in FIG. 3 are denoted by the same reference numerals and will not be described further in detail.

The liquid crystal filter of this exemplary configuration has a correction liquid crystal cell 24 in the fourth layer of the liquid crystal filter of first exemplary configuration, as shown in FIG. 10. In the correction liquid crystal cell 24, the pair of glass substrates 12 and 13 has antiparallel orientation and liquid crystal molecules constituting the liquid crystal layer have homogeneous orientation. The pair of polarizers 14 and 15 has transmission axes orthogonal to each other. The direction of transmission axis of one polarizer (the polarizer on the lower side in FIG. 10) is arranged to form an angle of 135°±5° with the direction of orientation of the one substrate. As in the first exemplary configuration, the thickness of the liquid crystal layer in the first liquid crystal cell 21a is 6.5 μm. The thickness of the liquid crystal layer in the second liquid crystal cell 21b is 12.9 μm. The thickness of the liquid crystal layer in the third liquid crystal cell 21c is 25.8 μm. The thickness of the liquid crystal layer in the correction liquid crystal cell 24 is 16.1 μm.

Figure 12:
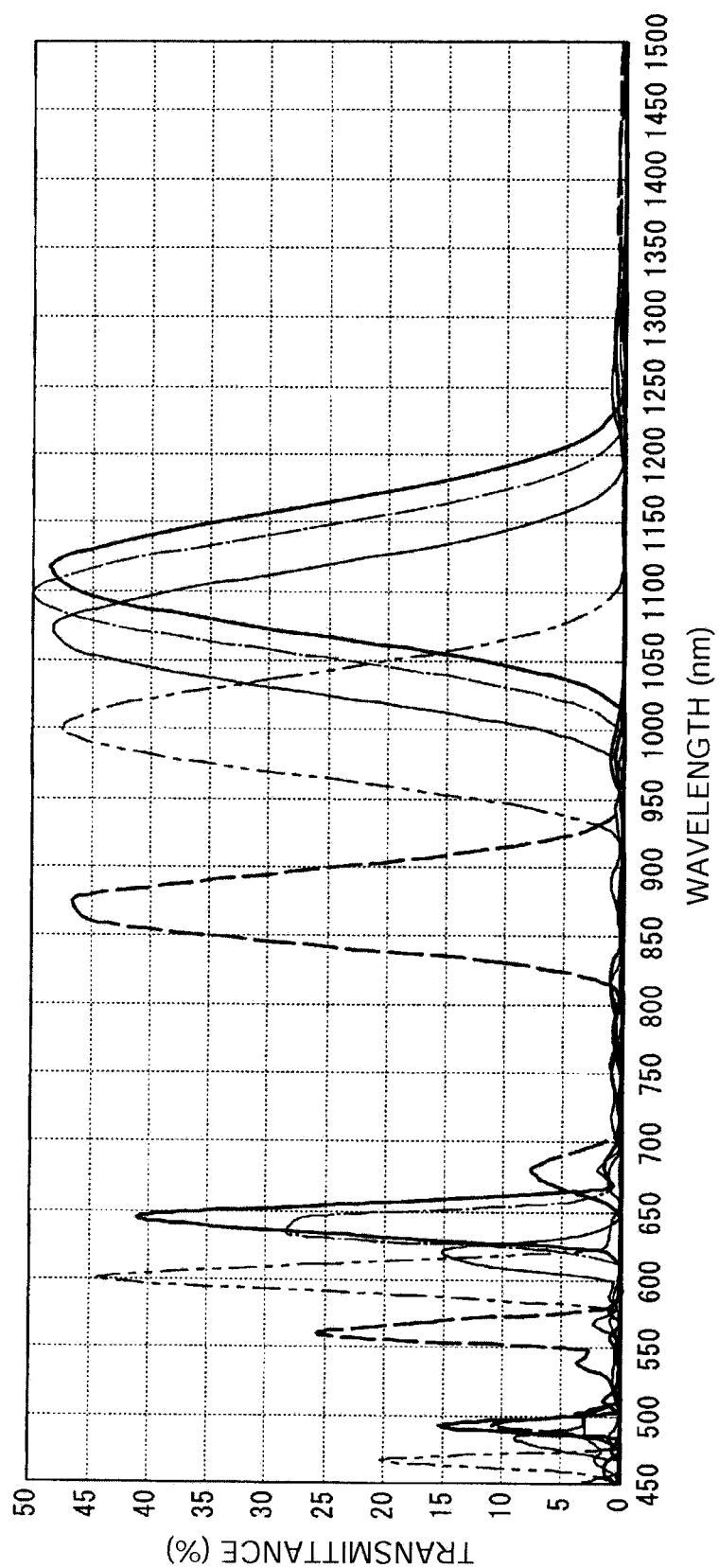
FIG. 12 shows spectroscopic properties of the liquid crystal filter.

With this exemplary configuration, a liquid crystal filter having spectroscopic properties shown in FIG. 12 and having a transmission wavelength range of 800 to 1200 nm can be realized. It can be understood that noise components of 700 nm or shorter are reduced, compared with the spectrum shown in FIG. 6 in the first exemplary configuration.

The exemplary configurations of the liquid crystal filter are described in the above sections of Liquid Crystal Filter-1 to Liquid Crystal Filter-6. However, the order of stacking plural sets of liquid crystal cells may be arbitrary.

Concentration Distribution Calculating Method

Next, a concentration calculating method by the DSP 6 will be described.

The DSP 6 reads out image data for each wavelength stored in the external memory 7 and detects the concentration of the marker on the basis of the image data and a data table that is stored in advance. This data table is equivalent to a calibration curve. The light intensity distribution of each pixel constituting the image data is collated with the correlation between light intensity and marker concentration in the data table, and the concentration of the marker is thus found. The correlation between light intensity and marker concentration is found in advance by a preparatory experiment and the data table is prepared. Meanwhile, instead of the method using the data table, multivariate analysis may be performed on the basis of data of light intensity distribution at each point and the marker concentration may thus be found. After that, the DSP 6 calculates the concentration of the drug from the concentration of the marker.

If the concentration of the drug is Cx, the concentration of the marker is Cm and the elapsed time after administration is t, the concentration Cx of the drug can be interpreted as the function of the concentration Cm of the marker and the elapsed time t. That is, the following holds.

$$Cx = f(Cm, t) \quad (9)$$

Specifically, for example, the following holds.

$$Cx = k(t) \times Cm + l(t) \quad (10)$$

In this case, after the mixture of the marker and the drug is administered to the living body, blood is collected at plural time points. The correlation between the elapsed time t, and the concentration Cm of the marker and the concentration Cx of the drug, is examined. From the result of the examination, k(t) and l(t) in the equation (10) are found. After that, if the concentration of the marker can be found by the above method, the concentration of the drug can be calculated from the equation (10) (calculation of concentration).

Figure 13:
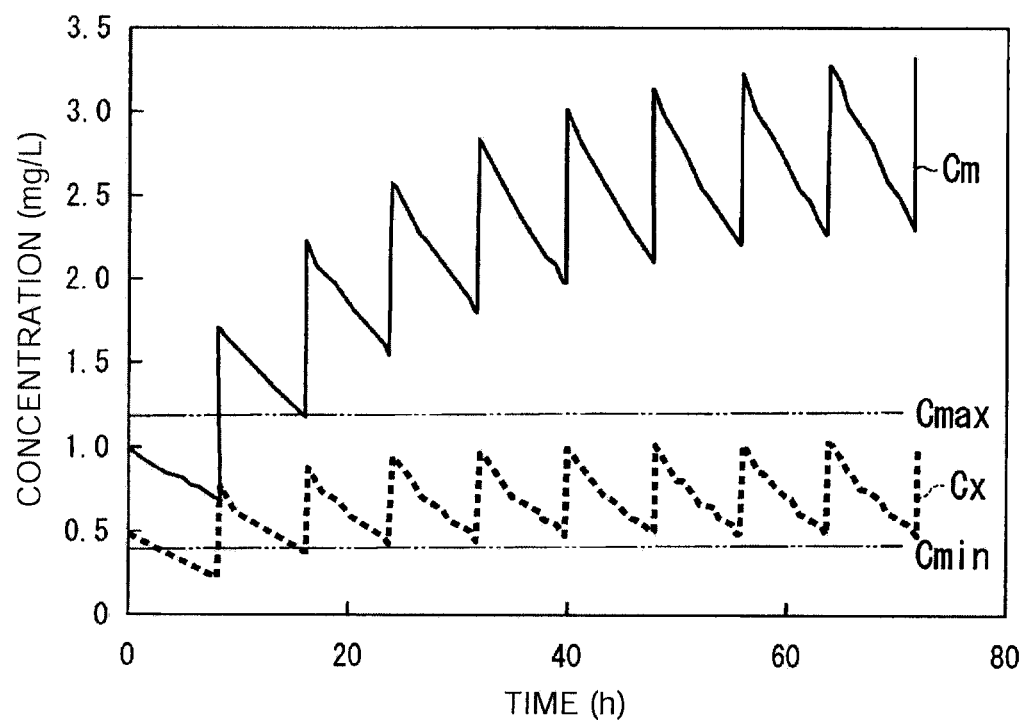
FIG. 13 is a graph showing the relation between marker concentration and drug concentration in the case where administration by intravenous injection is performed.
Figure 14:
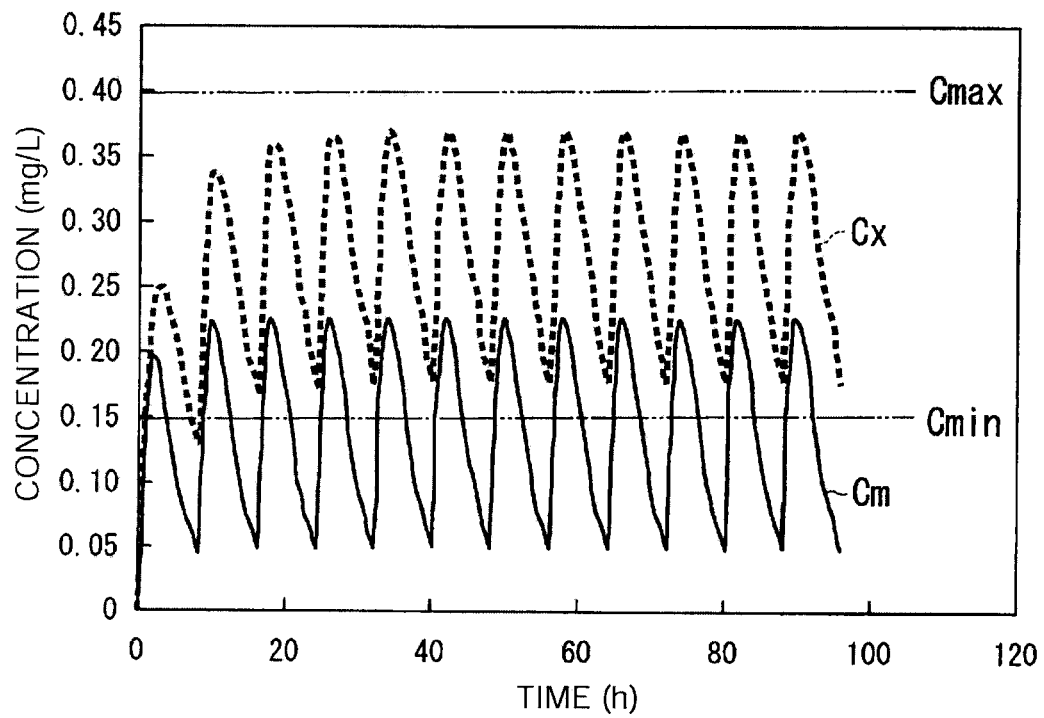
FIG. 14 is a graph showing the relation between marker concentration and drug concentration in the case where oral administration is performed.

For example, if the mixture of the marker and the drug is administered to the living body by intravenous injection every few hours, it is expected that the concentration of the marker and the drug changes as shown in FIG. 13 at a predetermined position in the living body. That is, when the user wants to control the concentration of the drug within a concentration control range Cmin to Cmax that is therapeutically effective without causing any side effects, the concentration Cm of the marker can be found by the above method and then the concentration Cx of the drug can be calculated, for example, from the equation (10). Thus, the change in the in vivo drug concentration Cx can be measured as shown in FIG. 13 and it can be determined whether the drug concentration is within the concentration control range or not. Similarly, if the mixture of the marker and the drug is orally administered every few hours, development as shown in FIG. 14 can be seen.

In the concentration distribution measuring device 1 according to this embodiment, the drug concentration is calculated from the intensity distribution of light in a predetermined wavelength range of, for example, about 800 to 1200 nm, instead of calculating the drug concentration solely on the basis of the intensity value of light having a specific wavelength. Therefore, the drug concentration can be accurately calculated. In this manner, with the concentration distribution measuring device 1 according to this embodiment, drug concentration distribution can be accurately and quickly measured by detecting emitted light from the living body, using a non-invasive technique without performing blood collection and so on.

A medical technique called therapeutic drug monitoring (TDM) is known in which the drug concentration in blood of individual patients is measured and thus usage and dosage are designed to make the drug concentration reach a desirable effective therapeutic concentration. The concentration distribution measuring device 1 according to this embodiment can measure the drug concentration in real time and therefore can be utilized for the TDM technique, not only in administration routes having long administration intervals (for example, three to six hours) as with oral medicine, but also in instantaneous administration routes including nasal administration, pulmonary administration and intravenous injection. Moreover, two-dimensional concentration distribution data can be acquired, whereas in the traditional technique using blood collection, concentration data can only be obtained at one point in a vein. Therefore, the range of information acquired is expanded and the measuring accuracy is significantly improved. The range of application of the technique is substantially broadened.

Furthermore, the idea of TDM can also be applied to drugs which are not administered and monitored because such administration and monitoring is traditionally considered to take long measuring time and hence be uneconomical. In this manner, the effects of various drugs can be substantially achieved without causing any side effects. Therefore, drugs that are difficult to use for reasons such as having significant side effects while exerting substantial pharmacological effects, or having a narrow effective concentration range, can become easier to use. Thus, according to this embodiment, the quality of medical services can be improved and the cost of medical services can be reduced, which can greatly contribute to society.

It should be noted that the technical scope of the invention is not limited to the above embodiment and various changes and modifications can be made without departing from the scope of the invention. For example, while the example of administering a mixture of a marker and a drug to a living body is described in the embodiment, if a drug having an imaging function can be administered to the living body, there is no need to use a marker. In this case, if a data table describing the correlation between light intensity and drug concentration is prepared, concentration distribution of the drug can be directly found, by using the data table, directly from the data of light intensity distribution of each pixel on the measuring target.

Although the example of using a mixture of one kind of marker and a drug is described in the embodiment, the marker is not limited to one kind and a mixture of plural kinds of markers and a drug may also be used. For example, if two kinds of markers are used, two data tables (calibration curves) can be prepared, that is, a data table showing the correlation between light intensity distribution and marker concentration with respect to a first marker and a data table showing the correlation between light intensity distribution and marker concentration with respect to a second marker. Then, if the concentration of the drug is Cx, the concentration of the first marker is Cm1, the concentration of the second marker is Cm2 and elapsed time after administration is t, the concentration Cx of the drug can be interpreted as the function of the concentration Cm1 of the first marker, the concentration Cm2 of the second marker and the elapsed time t. That is, the following holds.

$$Cx = f(Cm1, Cm2, t) \quad (11)$$

Specifically, for example, the following holds.

$$Cx = k(t) \times Cm1 + l(t) \times Cm2 + m(t) \quad (12)$$

In this case, after the mixture of the first and second markers and the drug is administered, blood is collected at plural time points and the correlation between the elapsed time t, and the concentrations Cm1 and Cm2 of the first and second markers and the concentration Cx of the drug, is examined. From the results of the examination, k(t), l(t) and m(t) in the equation (12) are found. After that, if the concentration of the markers can be found by the method described in the above embodiment, the concentration of the drug can be calculated from the equation (12).

Figure 15:
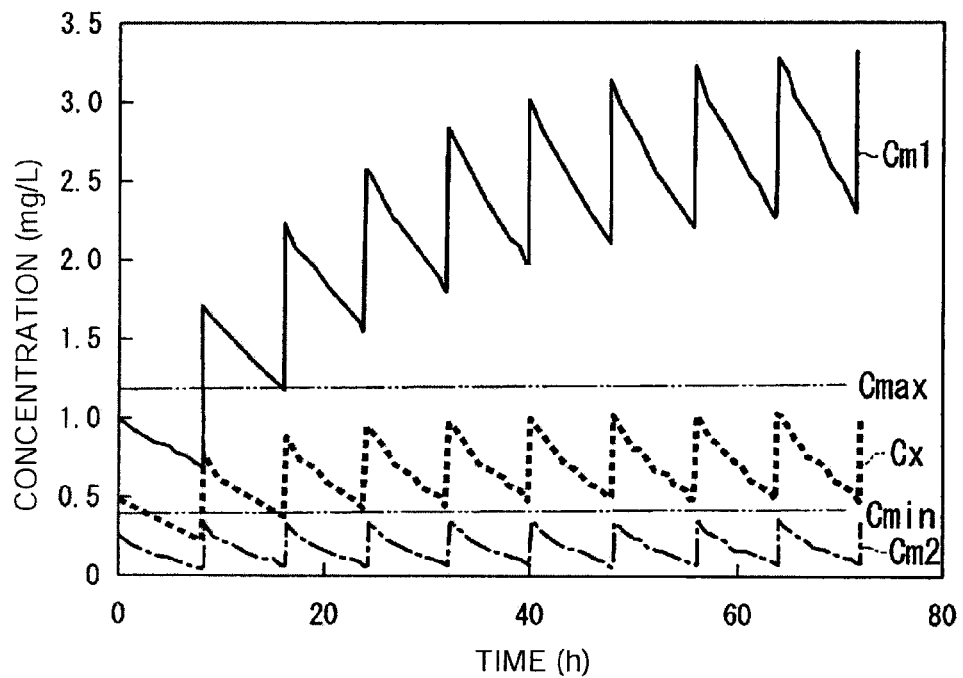
FIG. 15 is a graph showing the relation between concentration of two kinds of markers and drug concentration in the case where administration by intravenous injection is performed.
Figure 16:
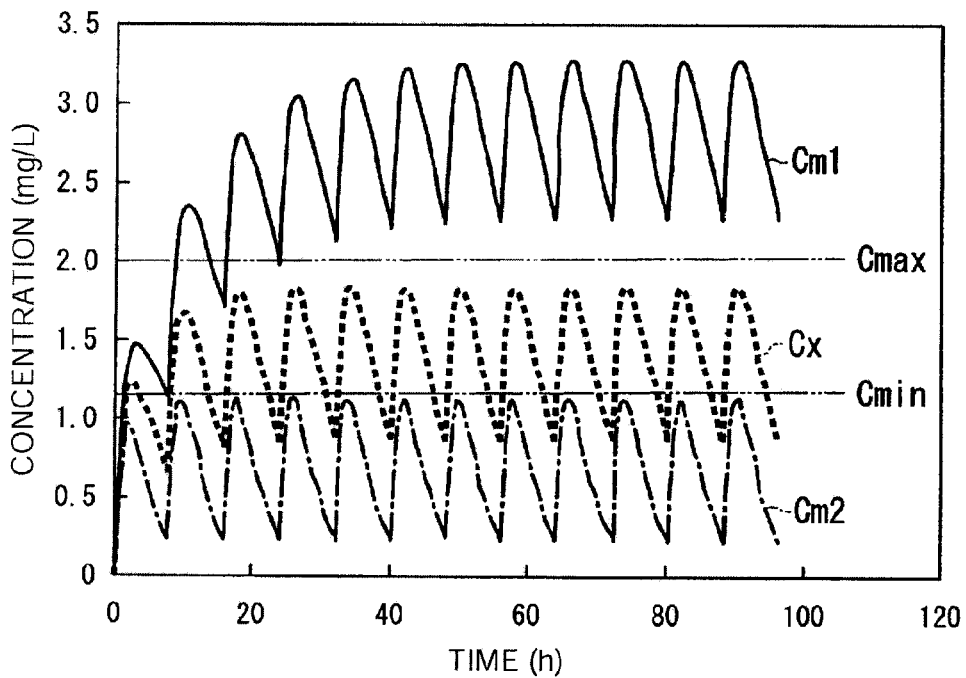
FIG. 16 is a graph showing the relation between concentration of two kinds of markers and drug concentration in the case of oral administration.

For example, if the mixture of the first and second markers and the drug is administered to the living body by intravenous injection every few hours, it is expected that the concentration of the first and second markers and the drug changes as shown in FIG. 15 at a predetermined position in the living body. That is, when the user wants to control the concentration of the drug within a concentration control range Cmin to Cmax that is therapeutically effective without causing any side effects, the concentrations Cm1 and Cm2 of the first and second markers can be found by the above method and then the concentration Cx of the drug can be calculated, for example, from the equation (12). Thus, the change in the in vivo drug concentration Cx can be measured as shown in FIG. 15 and it can be determined whether the drug concentration is within the concentration control range Cmin to Cmax or not. Similarly, if the mixture of the first and second markers and the drug is orally administered every few hours, development as shown in FIG. 16 can be seen.

For example, it is conceivable that the markers and the drug show different behaviors in the living body, such as which position in the living body the markers and the drug tend to be accumulated at. In view of this point, it is possible to calculate the drug concentration in a more practical way by calculating the drug concentration from the concentration of plural kinds of markers rather than calculating the drug concentration from the concentration of one kind of marker.

FIG. 2 described in the embodiment shows an illustration in which a relatively large concentration distribution measuring device is arranged at a position distant from the living body. However, a small device that only measures a part of the body may be used. For example, a device equipped with a light source, a liquid crystal filter, a CCD or the like may be directly attached to skin just like a wrist watch.

What is claimed is:

1. An in vivo drug concentration distribution measuring method comprising:
    administering a marker having an imaging function and a drug to a living body;
    casting light to the living body as a measuring target;
    when the light is cast to the marker from outside of the living body, detecting intensity of light of a predetermined wavelength range emitted from plural positions on the measuring target using a photodetector, of the light emitted to outside of the living body from the marker, and repeating the detection of the intensity a plurality of times using the photodetector while changing the predetermined wavelength range with a variable-wavelength filter that is operable to scan an entire wavelength range of the light emitted to outside of the living body from the marker, thereby acquiring intensity distribution of the light emitted from the plural positions on the measuring target; and
    calculating a concentration of the drug administered with the marker in accordance with the intensity distribution of the light at the plural positions on the measuring target,
    wherein the variable-wavelength filter has a plurality of liquid crystal cells, each cell including a pair of polarizers, a liquid crystal layer inserted between the pair of polarizers, and an electrode which applies a voltage to the liquid crystal layer.

2. The in vivo drug concentration distribution measuring method according to claim 1, wherein in the administration, plural kinds of the markers are administered to the living body, in the intensity distribution acquisition, the intensity distribution of the light emitted from the plural positions on the measuring target is acquired for each of the plural kinds of the markers, and in the concentration calculation, the concentration of the drug is calculated in accordance with the intensity distribution of the light at the plural positions on the measuring target corresponding to the plural kinds of the markers.

3. The in vivo drug concentration distribution measuring method of claim 1, wherein a thickness of each liquid crystal layer of each liquid crystal cell is different.

4. The in vivo drug concentration distribution measuring method of claim 1, wherein a voltage applied to each of the liquid crystal cells is cycled through a plurality of voltages to obtain the intensity distribution.

5. An in vivo drug concentration distribution measuring device for measuring, when a drug having an imaging function is administered, in vivo concentration distribution of the drug, the device comprising:
 a light source configured to cast light to a living body as a measuring target;
 a variable-wavelength filter, the variable-wavelength filter being configured to:
  receive, after the light is cast to the drug from outside of the living body, light emitted from the drug to outside of the living body as incident light,
  scan an entire wavelength range of the incident light;
  transmit light of a predetermined wavelength range, of the entire wavelength range of the incident light, and change the predetermined wavelength range;
 a photodetector unit configured to detect an intensity of the incident light passing through the variable-wavelength filter and acquire an intensity distribution of light emitted from plural positions on the measuring target; and
 a drug concentration calculating unit configured to calculate a concentration of the drug in accordance with the intensity distribution of the light at the plural positions on the measuring target acquired by the photodetector unit,
 wherein the variable-wavelength filter has a plurality of liquid crystal cells, each cell including a pair of polarizers, a liquid crystal layer inserted between the pair of polarizers, and an electrode which applies a voltage to the liquid crystal layer.

6. The in vivo drug concentration distribution measuring device according to claim 5, wherein an optical filter which interrupts light having a wavelength of 650 nm or shorter is provided on a light incident side of the photodetector unit.

7. The in vivo drug concentration distribution measuring device of claim 5, wherein a thickness of each liquid crystal layer of each liquid crystal cell is different.

8. The in vivo drug concentration distribution measuring device of claim 5, wherein a voltage applied to each of the liquid crystal cells is cycled through a plurality of voltages to obtain the intensity distribution.

* * * * *